United States Patent
Karavitis

(10) Patent No.: US 9,913,688 B1
(45) Date of Patent: Mar. 13, 2018

(54) SPLIT PULSE PICOSECOND LASER FOR TATTOO REMOVAL

(71) Applicant: Cutera, Inc., Brisbane, CA (US)

(72) Inventor: Michael Karavitis, San Pedro, CA (US)

(73) Assignee: Cutera, Inc., Brisbane, CA (US)

( * ) Notice: Subject to any disclaimer, the term of this patent is extended or adjusted under 35 U.S.C. 154(b) by 322 days.

(21) Appl. No.: 14/495,829

(22) Filed: Sep. 24, 2014

Related U.S. Application Data

(60) Provisional application No. 61/885,170, filed on Oct. 1, 2013.

(51) Int. Cl.
*A61B 18/20* (2006.01)

(52) U.S. Cl.
CPC ................... *A61B 18/20* (2013.01)

(58) Field of Classification Search
CPC ............. A61B 18/18; A61B 18/20; A61B 2018/2045–2018/2055; A61N 1/30; H01S 3/10; H01S 3/115; H01S 3/13
USPC .......... 606/4, 2–2.5, 9–13, 16–18; 372/30, 372/10–17, 20, 700, 25–8; 607/88–91; 128/898
See application file for complete search history.

(56) References Cited

U.S. PATENT DOCUMENTS

| | | | |
|---|---|---|---|
| 5,312,396 A * | 5/1994 | Feld .................... | A61B 18/245 606/10 |
| 6,373,864 B1 | 4/2002 | Georges et al. | |
| 7,929,579 B2 * | 4/2011 | Hohm .................. | A61B 18/203 372/12 |
| 9,504,849 B2 * | 11/2016 | Yoo ....................... | A61N 5/0624 |
| 2005/0172852 A1 * | 8/2005 | Anderson .............. | C09D 11/50 106/31.03 |
| 2008/0031288 A1 | 2/2008 | Sierra et al. | |
| 2009/0292277 A1 | 11/2009 | Sierra et al. | |
| 2010/0135347 A1 * | 6/2010 | Deladurantaye .... | H01S 3/06754 372/30 |
| 2010/0296531 A1 | 11/2010 | Hohm et al. | |
| 2014/0243804 A1 * | 8/2014 | Lukac .................. | A61B 18/203 606/9 |
| 2015/0080863 A1 | 3/2015 | Welches et al. | |

OTHER PUBLICATIONS

Brauer et al., "Successful and Rapid Treatment of Blue and Green Tattoo Pigment With a Novel Picosecond Laser", Arch Dermatol, vol. 148 No. 7, Jul. 2012, pp. 820-823.

Herd et al., "A Clinical and Histologic Prospective Controlled Comparative Study of the Picosecond Titanium: Sapphire (795 Nm) Laser Versus the Q-Switched Alexandrite (752 Nm) Laser for Removing Tattoo Pigment", Journal of the American Academy of Dermatology, vol. 40, No. 4, Apr. 1999, pp. 603-606.

(Continued)

*Primary Examiner* — Lynsey Eiseman
*Assistant Examiner* — Jonathan Kuo
(74) *Attorney, Agent, or Firm* — Morrison & Foerster LLP

(57) ABSTRACT

A method of removing tattoos or pigmented lesions by generating at least two laser pulses having a pulse width in the picosecond range, where the peak power of each pulse is less than 15 GW/cm$^2$ and where the spacing between the pulses is less than ten nanoseconds, and directing the pulses to the tattoo or pigmented lesion to be removed.

8 Claims, 2 Drawing Sheets

(56) References Cited

OTHER PUBLICATIONS

Ho et al., "Laser-Tattoo Removal—A Study of the Mechanism and the Optimal Treatment Strategy via Computer Simulations", Lasers in Surgery and Medicine, vol. 30, 2002, pp. 389-397.
Isyanova et al., "High-Power, Passively Q-Switched Microlaser—Power Amplifier System", OSA TOPS vol. 50, Advanced Solid-State Lasers, 2001, pp. 186-190.
Izikson et al., "Safety and Effectiveness of Black Tattoo Clearance in a Pig Model After a Single Treatment With a Novel 758nm 500 Picosecond Laser: A Pilot Study", Lasers in Surgery and Medicine, vol. 42, 2010, pp. 640-646.
Karsai et al., "Treatment of Resistant Tattoos Using a New Generation Q-Switched Nd:YAG Laser: Influence of Beam Profile and Spot Size on Clearance Success", Lasers in Surgery and Medicine, vol. 40, 2008, pp. 139-145.
Kent et al., "Laser Tattoo Removal: A Review", Dermatologic Surgery, vol. 38, No. 1, Jan. 2012, pp. 1-13.
Ross et al., "Comparison of Responses of Tattoos to Picosecond and Nanosecond Q-Switched Neodymium:YAG Lasers", Arch Dermatol., vol. 134, Feb. 1998, pp. 167-171.
Rusen et al., "Picosecond Laser System Based on Microchip Oscillator", Journal of Optoelectronics and Advanced Materials, vol. 10, No. 11, Nov. 2008, pp. 3022-3028.
Saedi et al., "Treatment of Tattoos With a Picosecond Alexandrite Laser", Arch Dermatol., vol. 148, No. 12, Dec. 2012, pp. 1360-1363.
Shargorodsky et al., "Laser System for SLR with a Diode-Pumped Microlaser used as a Master Oscillator", 12th International Workshop on Laser Ranging, Nov. 13 to 17, 2000, pp. 1-3.
Vogel et al., "Intraocular Photodisruption With Picosecond and Nanosecond Laser Pulses: Tissue Effects in Cornea, Lens, and Retina", Investigative Ophthalmology & Visual Science, vol. 35, No. 7, Jun. 1994, pp. 3032-3044.
Zysset et al., "Picosecond Optical Breakdown: Tissue Effects and Reduction of Collateral Damage", Lasers in Surgery and Medicine, vol. 9, 1989, pp. 193-204.
Stratan et al., "Picosecond Laser System Based on Microchip Oscillator", Journal of Optoelectronics and Advanced Materials, vol. 10, No. 11, Nov. 2008, pp. 3022-3028.

* cited by examiner

SPLIT PULSE PICOSECOND LASER FOR TATTOO REMOVAL

CROSS-REFERENCE TO RELATED APPLICATIONS

This application claims priority to U.S. Provisional Application Ser. No. 61/885,170 filed Oct. 1, 2013, which is incorporated herein by reference in its entirety for all purposes.

FIELD

This application generally relates to methods of removing tattoos and pigmented lesions using laser irradiation. More specifically, this application relates to methods for using picosecond laser pulses for tattoo and pigmented lesion removal.

BACKGROUND

Tattoo removal using picosecond laser pulses ($<10^{-9}$ seconds) has been demonstrated as far back as 1998. In an initial study, picosecond laser pulses were shown to clear tattoos more effectively than their nanosecond counterparts at equal fluences (0.65 J/cm$^2$). However, the use of picosecond laser pulses for tattoo removal was initially limited by the relatively low power of picosecond lasers, and subsequently by the potential for tissue damage using higher-powered picosecond lasers. Methods for using picosecond lasers to remove tattoos or pigmented lesions that can achieve higher fluence levels without tissue damage may be desirable.

SUMMARY

A method of treating tattoos or pigmented lesions includes generating at least two laser pulses having a pulse width in the picosecond range. The peak power of each pulse is less than 5 GW/cm$^2$. The spacing between the pulses is less than ten nanoseconds and preferably less than two nanoseconds. The pulses are directed to the tattoo or lesion to be removed.

DESCRIPTION OF THE FIGURES

For a better understanding of the various described embodiments, reference should be made to the Detailed Description below, in conjunction with the following drawings.

DETAILED DESCRIPTION

Figure 1:
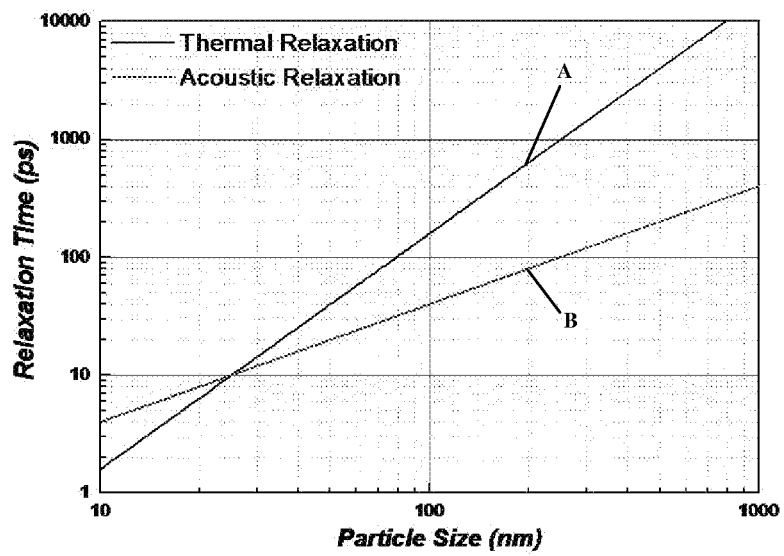
FIG. 1 depicts thermal and acoustic relaxation times as a function of particle size.

The following detailed description is of the best currently contemplated modes of carrying out the invention. The description is not to be taken in a limiting sense, but is made merely for the purpose of illustrating the general principles of the invention, since the scope of the invention is best defined by the appended claims.

As discussed above, an initial study indicated that picosecond laser pulses can clear tattoos more effectively than their nanosecond counterparts at equal fluences. Several follow-on studies confirmed these findings. The limiting factor ubiquitous to all of these studies was the energy output of the picosecond lasers, all of which were severely underpowered for this application. In fact, the laser fluences used in these studies were a fraction of that produced by nanosecond Q-switched lasers used for tattoo removal. It is common for dermatologists to use in excess of 6 J/cm$^2$ with nanosecond laser tattoo removal. It is assumed that the picosecond studies were performed at low power levers due to the power limitations imposed by picosecond lasers available at the time of the studies.

Recent advances in ultrafast technology have enabled construction of a picosecond class laser (pulse duration <900 ps FWHM) that can produce energy levels comparable to the nanosecond lasers physicians currently use for tattoo removal. Unfortunately, for laser pulses in this temporal range, the fluences used for treating tattoos are restricted to under 2 J/cm$^2$ due to the onset of adverse events (purpura, pinpoint petechiae, hyperpigmentation, edema, erythema, bruising) associated with the enormous peak powers characteristic of ultrashort pulses of light. The adverse event profile serves to restrict the amount of power that can effectively be coupled into a tattoo and is presumably associated with the formation of plasma caused by the high intensity of the electric field generating free electrons in the epidermis as well as dermis. Plasma formation is highly intensity dependent. The onset of plasma formation occurs at a distinct threshold, above which, the adverse event profile increases geometrically with laser pulse intensity. Thus, operating at laser pulse intensities below the threshold for plasma formation is critical for successful treatment of skin conditions using picosecond laser pulses.

At first blush, it would appear that due to the energy limitations of picosecond pulses, nanosecond lasers may be better suited for tattoo or pigmentation removal. There are, however, two potential mechanisms which lead to tattoo clearing induced by pulses of light. The first mechanism is thermal. This involves the heating of the tattoo ink particles which leads to the generation of steam. The steam serves to create cavitation thereby fragmenting the tattoo particle into smaller pieces which may then be removed by macrophage activity. The second mechanism is photoacoustic, and involves the generation of a pressure wave inside of the ink particle. When the force exerted by the pressure wave exceeds the tensile strength of the ink particle, the particle shatters which again results in fragmentation and subsequent removal via macrophage activity. Similar mechanisms may apply to removal of pigmented lesions, such as those caused by melanin in melanosomes.

In order for either of the above mechanisms to be active in the tattoo clearing process, the pulse duration must be less than the characteristic relaxation time for the given process. For the photothermal process, the relaxation time scales quadratically with particle diameter, and for the photoacoustic process, the relaxation time scales linearly with particle diameter. FIG. 1 shows the characteristic relaxation times for both the photothermal (curve A) as well as photoacoustic processes (curve B) as a function of particle size for a typical carbon based tattoo ink. Typical particle sizes in tattoo ink range from 10 nm-100 nm in diameter with the largest conglomerates approaching 1 μm. This sets an upper limit on the thermal relaxation time to 10 ns, well within the range of most commercial Q-switch lasers. On the other hand, the acoustic relaxation (confinement) time is significantly shorter across the boards. For the largest tattoo conglomerates, the photoacoustic confinement time is on the order of 500 picoseconds. Since the overwhelming majority of commercial Q-switch lasers produce pulses longer than 5 ns, the acoustic mechanism is not efficiently driven by these devices. This suggests that picosecond laser pulses may have added benefits in the ink clearing process if the energy of the pulses could be appropriately scaled up to efficacious levels.

Figure 2:
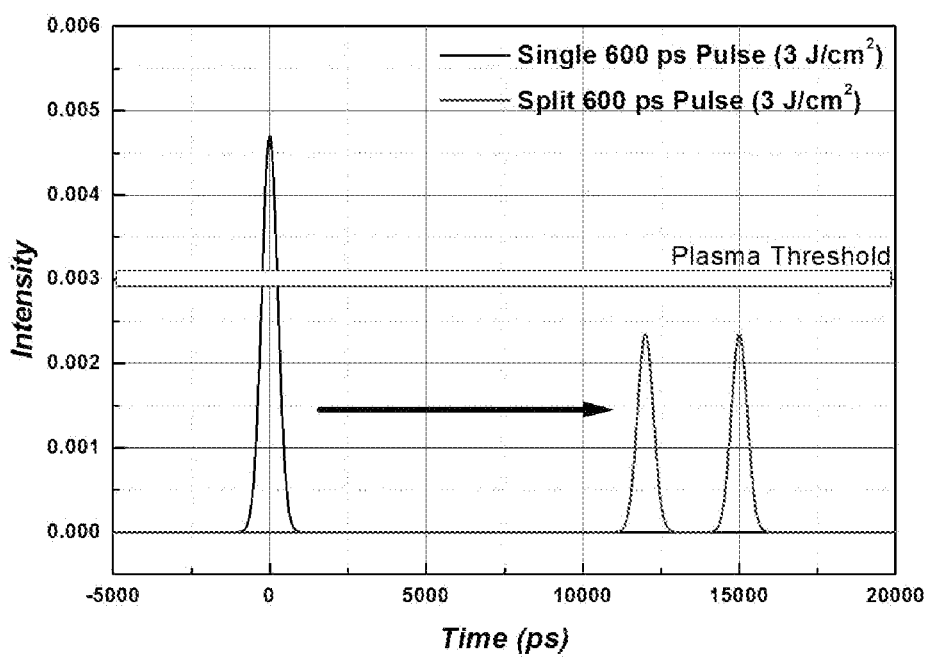
FIG. 2 depicts splitting a single, high-intensity pulse into two lower-intensity sub-pulses.

The strategy proposed herein is to split the picosecond laser pulse into two or more smaller laser pulses (subpulses) separated by a time delay as shown in FIG. 2. For a given tattoo ink, plasma formation occurs at a threshold intensity (illustrated by the box at the 0.003 marker in FIG. 2). As long as the peak intensity is below the plasma threshold, adverse events are minimized. Also pictured in FIG. 2, are a single picosecond laser pulse (left hand side of FIG. 2) as well as a "split" picosecond laser pulse (right hand side of FIG. 2). The combined fluence of the two smaller pulses in the split pulse format is designed to be equal to the fluence of the single pulse (e.g. 3 J/cm$^2$). The "split" pulse clearly delivers lower peak intensity (below the plasma threshold) at equal fluence to the single pulse which exceeds the plasma threshold. Thus, the split pulse format succeeds in increasing the amount of energy the system can deliver to a given tattoo while simultaneously maintaining the picosecond pulse duration necessary to drive the photoacoustic mechanism of ink particle fragmentation.

Figure 3:
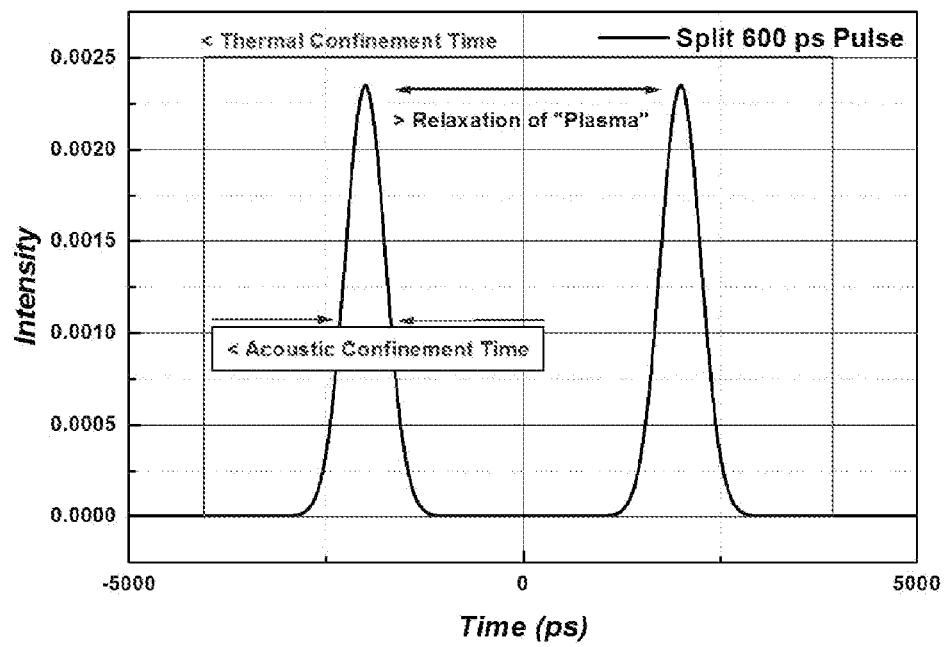
FIG. 3 depicts thermal and acoustic confinement times associated with two pulses.

The timing details of the split pulse format, shown in FIG. 3, have two constraints. First, as mentioned previously, the individual pulses, must be shorter than the acoustic relaxation (confinement) time of the ink particles or pigmented lesions. For carbon based ink, this is typically less than a nanosecond in duration. Second, the pulse separation needs to be less than the thermal confinement time of the particle to be removed. Again, for carbon based ink particles of one micron in diameter, the relaxation time is ten nanoseconds. For pigments, melanin, or melanosomes, the diameter may be a few microns, (e.g., 2-4 microns) with a correspondingly much higher relaxation time due to quadratic scaling.

Keeping the following in mind, the "split" pulse format should have the following characteristics:

(1) The "split" pulse format should be made up of two or more pulses separated in time where the pulse duration of the sub-pulses is shorter than the acoustic confinement time of tattoo ink particles to take full advantage of the photoacoustic mechanism in tattoo ink particle fragmentation. There may be advantages across the full picosecond range. Performance may be optimized in the 200 to 900 ps range and most preferably in the 600 to 800 ps range. For example, a pulse duration of 600, 650, 700, 750, or 800 picoseconds may be particularly effective.

(2) The intensity of the sub-pulses should be below the plasma or ionization threshold of the ink particles; however, the cumulative fluence of the pulse train should be equivalent to what is currently used for tattoo removal using nanosecond systems. In initial experiments with this method, it has been found that damage can begin to occur when the fluence is 3-4 J/cm$^2$ for 700 picosecond pulses. This corresponds to about 4 to 5 GW/cm$^2$. However, under some circumstances, the fluence can go higher without resulting in damage; for example, fluences of 6-10 J/cm$^2$ (corresponding to 5 to 15 GW/cm$^2$) may be possible, depending on the characteristics of the skin and tattoo or pigment to be treated. For example, a light-skinned person with a relatively faint tattoo may be able to receive a fluence at the higher end of the range without damage.

(3) The temporal separation of sub-pulses should shorter than the thermal confinement time of tattoo ink particles or pigmented lesions to take full advantage of the role the thermal mechanism plays in particle fragmentation. For example, the separation may range from 1 to 10 nanoseconds and is preferably less than 2.0 ns. In some embodiments, the separation may be more effective at 1.0 ns. 1.3 ns, 1.5 ns, 1.8 ns, or 2.0 ns.

The invention is not limited to two smaller pulses. A train of pulses can be used. In addition, bursts of two, three or four pulses could be used where the spacing between all the pulses in the burst are shorter than the thermal confinement time. In some embodiments, a single activation of a treatment laser (e.g., via a foot pedal) may deliver multiple bursts of pulses, at a rate of up to 10 bursts per second (10 Hz).

Figure 4:
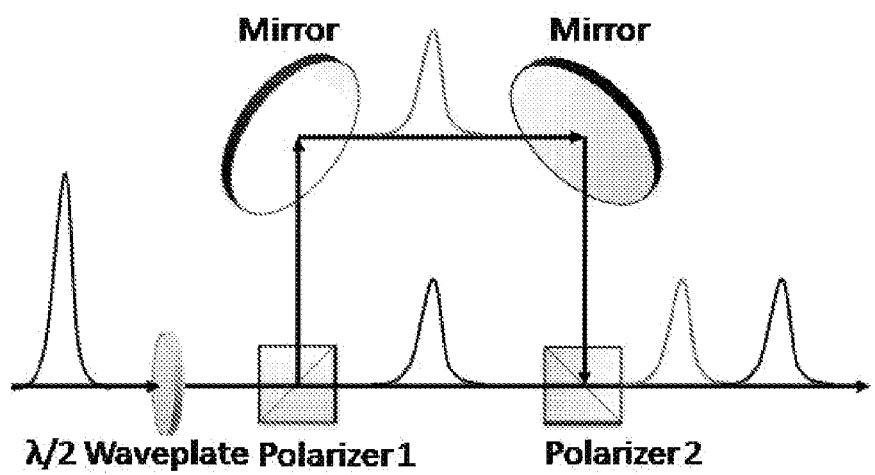
FIG. 4 depicts an exemplary optical train for splitting a single high-intensity laser pulse into two lower-intensity pulses.

FIG. 4 illustrates a simple, low cost optical arrangement that is capable of producing a "split" pulse train. First, a single pulse passes through a λ/2 waveplate, which alters the polarization of the pulse such that polarizer 1 splits the pulse into a transmitted component and a reflected component of equal intensity. The transmitted pulse passes through a second polarizer (2), while the reflected pulse is sent to an assembly of mirrors (either curved or flat). The mirror assembly directs the pulse to polarizer 2, but after introducing a significant path length differential relative to the transmitted pulse. The reflected pulse and transmitted pulse are recombined at polarizer 2, and remain spatially coincident after that optical train.

The path length difference between the two arms in the optical assembly mentioned above is responsible for generating the temporal delay. Light travels approximately one foot per nanosecond, so an optical delay of 1 ns to 10 ns would require a double pass path length differential of between 6 inches to 70 inches. In order to accommodate the larger delays, a multipass delay line, such as a Herriot Cell or White Cell could be inserted into reflected beam path. Also, if the mirrors in the reflected path are attached to a motorized actuator or translation stage, the path length could be dynamically adjusted leading to a variable temporal separation in sub-pulses. This parameter could be made adjustable by the user.

In some embodiments, the pulses may be passed through an optical amplifier to increase the laser power. Because the amplifier may amplify the first pulse more than the second pulse, it may be desirable for the first pulse to arrive at the amplifier with a lower power than the second pulse, such that the amplified pulses have roughly equal power. For this purpose, a variable retarder may be used as the waveplate for adjusting the relative power between the pulses.

There are a number of commercially available lasers that generate picosecond pulses. The pulse output can be divided into subpulses as discussed above. A preferred form of picosecond laser is based on a microchip oscillator. An example of such a laser system is disclosed in "Picosecond laser system based on microchip oscillator," Stratan, et. al., JOURNAL OF OPTOELECTRONICS AND ADVANCED MATERIALS Vol. 10, No. 11, November 2008, p. 3022-3028, incorporated herein by reference.

In some embodiments, the laser gain medium may be an Nd:YAG crystal with an output wavelength of 1064 nm. This output may be passed through a frequency doubler to generate a wavelength of 532 nm. Either wavelength (1064 or 532 nm) may be used for the above-described treatment.

It should be appreciated that the various features of the embodiments that have been described may be combined in various ways to produce numerous additional embodiments.

Accordingly, the invention is not to be limited by those specific embodiments and methods described herein.

What is claimed is:

1. A method of treating tissue by fragmenting ink particles in a tattoo using picosecond laser pulses generated by a laser system, each of said initial picosecond pulses having an initial pulse width between 200 and 900 picoseconds and being capable of creating a first peak power density, said method comprising:
   (a) dividing an initial picosecond pulse into at least two subpulses, each subpulse having the same pulse width as the initial pulse width, and wherein the spacing between the divided subpulses is between one nanosecond and ten nanoseconds; and
   (b) directing the subpulses to the tissue to be treated with the power density created by each subpulse being less than the first peak power density and with the pulse width and the power density of each pulse being selected to fragment ink particles.

2. A method as recited in claim 1, wherein steps (a) and (b) are repeated a plurality of times.

3. A method as recited in claim 1, wherein the width of each subpulse is between 600 and 800 picoseconds.

4. A method as recited in claim 1, wherein the laser pulses have a wavelength of 1064 nm.

5. A method as recited in claim 1, wherein the laser pulses have a wavelength of 532 nm.

6. A method as recited in claim 1, wherein the spacing between divided subpulses is less than 2 nanoseconds.

7. A method as recited in claim 1, wherein the peak power density created by each of the subpulses is between 5 and 15 $GW/cm^2$.

8. A method as recited in claim 1 wherein the first peak power density is 15 $GW/cm^2$.

* * * * *